(12) United States Patent
Schmidt et al.

(10) Patent No.: US 6,497,689 B1
(45) Date of Patent: Dec. 24, 2002

(54) DEVICE FOR HANDLING BODY LIQUIDS WHICH TRANSPORTS BODY LIQUID BY SIPHONING

(75) Inventors: Mattias Schmidt, Idstein (DE); Bruno Johannes Ehrnsperger, Frankfurt (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/720,223
(22) PCT Filed: Jun. 29, 1999
(86) PCT No.: PCT/US99/14648
§ 371 (c)(1),
(2), (4) Date: Dec. 20, 2000
(87) PCT Pub. No.: WO00/00141
PCT Pub. Date: Jan. 6, 2000
(51) Int. Cl.[7] .................................................. A61F 13/15
(52) U.S. Cl. ................................. 604/385.01; 604/317
(58) Field of Search ...................... 604/317; 2/400–406

(56) References Cited

U.S. PATENT DOCUMENTS 5,078,709 A  *  1/1992  Siciliano
5,562,646 A  *  10/1996  Goldman et al.
5,599,335 A  *  2/1997  Goldman et al.

FOREIGN PATENT DOCUMENTS

FR      2702371  *  3/1993

* cited by examiner

Primary Examiner—Jeanette Chapman
(74) Attorney, Agent, or Firm—Ian S. Robinson; Matthew P. Fitzpatrick; Ken K. Patel

(57) ABSTRACT

The present invention relates to a process for handling body liquids comprising a step of transporting the body liquid by siphoning. The present invention also relates to devices which carry out such processes. The present invention further relates to devices for handling body liquids comprising a liquid transport member which is substantially geometrically saturated with liquid.

17 Claims, 3 Drawing Sheets

Top View

Side View

DEVICE FOR HANDLING BODY LIQUIDS WHICH TRANSPORTS BODY LIQUID BY SIPHONING

CROSS REFERENCE

This application claims priority to PCT International Application Serial No. PCT/US99/14648 filed on Jun. 29, 1999 which claims priority to PCT International Application Serial No. PCT/US98/13449 filed on Jun. 29, 1998, PCT International Application Serial No. PCT/US98/13497 filed on Jun. 29, 1998, PCT International Application Serial No. PCT/US98/13521 filed on Jun. 29, 1998, and PCT International Application Serial No. PCT/US98/13523 filed on Jun. 29, 1998.

FIELD OF THE INVENTION

The present invention relates to a process for handling body liquids such as urine, sweat, saliva, blood, menses, purulence, or fecal material, and to devices carrying out such processes. The invention further relates to disposable absorbent articles such as baby diapers or training pants, adult incontinence products, and feminine hygiene products and other body liquid handling articles such as catheters, urinals, and the like.

BACKGROUND

Devices for handling body liquids are well known in the art and are frequently used for a wide variety of purposes. For example, the devices serve hygienic purposes such as diapers, sanitary napkins, adult incontinence products, underarm sweat pads, wound dressings, and the like. Accordingly such devices have been designed to cope with a large variety of different body liquids such as for example urine, sweat, saliva, blood, menses, purulence, fecal material, and the like.

Typically, it is desirable for such devices for handling body liquids to acquire the body liquid and at a first region of the device, transport the body liquid away from the zone of acquisition, and finally store the liquid in a second region, the designated liquid storage zone. The reasons for transporting the body liquid away from the zone of acquisition are manifold. These reasons include the creation of unwanted bulk close to the point of liquid discharge from the body and the avoidance of prolonged contact of the body liquids with the skin. The body liquid may either be transported in a direction perpendicular to the surface of the acquisition zone, i.e. into the bulk of the device, or the body liquids may be transported in a direction parallel to the surface of the acquisition zone and away from the point of acquisition. The transportation of liquid in these devices is typically achieved by means of capillary suction.

Capillary suction, however, has certain inherent limitations. In particular when it is desired to transport liquid against gravity, the capillary suction needs to be increased by decreasing the size of the capillaries. On the other hand, a capillary having a decreased pore size exhibits a higher resistance to liquid flow through the capillary. Hence, the combination of high capillary suction and high liquid flow rates can only be achieved by providing a large number of small capillaries which in turn leads to a large total cross-section of the device.

It has been suggested in PCT patent application WO 94/03214 (Lawrence) to remove liquid from the point of acquisition by means of siphoning. Therein, gravity or vacuum have been taught as the driving forces for liquid removal. Both driving forces, however, exhibit inherent disadvantages. When gravity is used as the driving force, the functionality of the device depends on its orientation in space, i.e. the storage region must always be lower than the acquisition region. Hence, applicability of liquid removal systems relying on gravity is limited. When vacuum is used as the driving force, a high mechanical effort is required to maintain the vacuum. Hence, in this case the complexity of the device limits the scope of possible applications. Furthermore, the liquid in this device is stored while still being relatively mobile which might create problems with respect to rewet and squeeze-out.

Hence, it is an object of the present invention to overcome the problems posed by the prior art devices for handling body liquids.

It is a further object of the present invention to provide a process for handling body liquids comprising a step of transporting the liquid by siphoning and a step of storing the liquid by either capillary or osmotic pressure.

It is a further object of the present invention to provide a device for handling body liquids which transports liquid by siphoning and which stores the liquid by either capillary or osmotic pressure.

It is a further object of the present invention to provide a device for handling body liquids comprising a liquid transport member which is substantially geometrically saturated before the intended use of the device.

It is a further object of the present invention to provide to a device for handling body liquids comprising liquid transport member which comprises free liquid before the intended use of the device.

SUMMARY OF THE INVENTION

The present invention provides a process for handling body liquids comprising the step of transporting the body liquids from an acquisition region to a storage region by siphoning. The step of transporting body liquid by siphoning comprises the steps of:

providing a liquid transport member being substantially geometrically saturated with liquid before the first step of acquiring liquid; the liquid saturating the liquid transport member being in liquid communication with the liquid acquisition region;

providing a liquid storage member in liquid communication with the liquid transport member, the liquid storage member being positioned inside the storage region;

acquiring liquid disposed onto the acquisition region into the liquid transport member;

replacing at least a portion of the liquid saturating the liquid transport member by the acquired liquid;

storing at least a portion of the replaced liquid in a storage member.

The process of the present invention is characterized in that the liquid is stored in a storage member by a means selected from the group of capillary pressure, osmotic pressure.

It is another aspect of the present invention to provide a device for handling body liquids designed to carry out the process of the present invention.

It is another aspect of the present invention to provide a device for handling body liquids having at least one liquid acquisition region and at least one liquid storage region. The storage region stores liquid by a means selected from the group of capillary pressure, osmotic pressure. The device for handling body liquids comprises a liquid transport member transporting liquid from the acquisition region to the liquid storage region. The device for handling body liquids of the present invention is characterized in that the liquid transport member is substantially geometrically saturated before the intended use of the device.

It is another aspect of the present invention to provide a device for handling body liquids having at least one liquid acquisition region and at least one liquid storage region. The storage region stores liquid by a means selected from the group of capillary pressure, osmotic pressure. The device for handling body liquids comprising a liquid transport member transporting liquid from the acquisition region to the liquid storage region. The device for handling of the present invention is characterized in that the liquid transport member is substantially geometrically saturated with free liquid.

DETAILED DESCRIPTION OF THE INVENTION

Process of Siphoning

Figure 1:
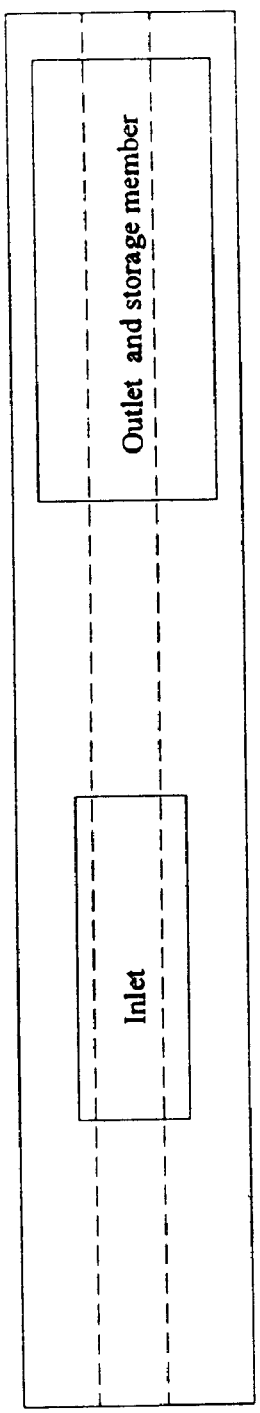
FIG. 1 is an illustration of one possible embodiment of the present invention and shows a top view of an absorbent article with a liquid acquisition member, liquid transportation member and a liquid storage member.
Figure 2:
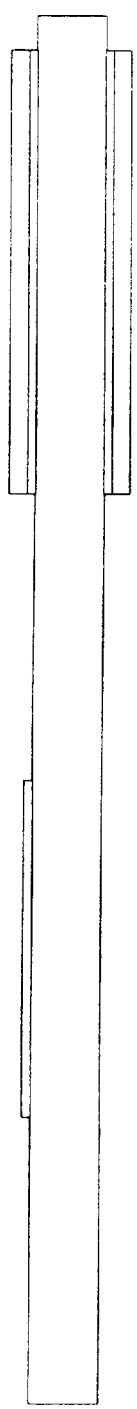
FIG. 2 is a side view of the absorbent article of FIG. 1.
Figure 3:
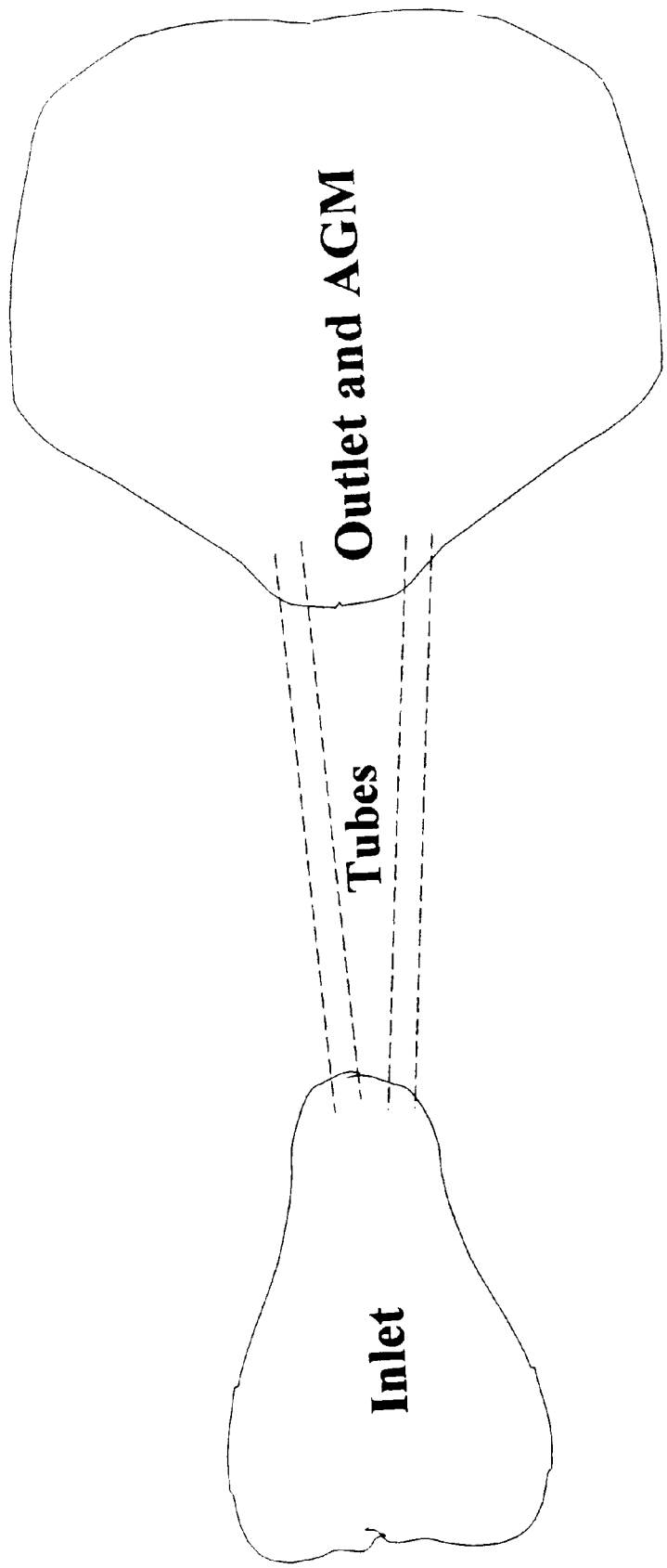
FIG. 3 is an illustration of another possible embodiment of the present invention and shows a liquid acquisition member, liquid transportation member and a liquid storage member which is comprised of AGM.

It is one aspect of the present invention to provide a process for transporting body liquids from an acquisition region to a storage region comprising a step of transporting the body liquid by siphoning.

The term "body liquids" as used herein refers to liquids and in particular aqueous liquids which are exudated or otherwise produced by the mammalian body at different locations of the body such as urine, sweat, saliva, blood, menses, purulence, fecal material, and the like. The term "device for handling body liquids" as used herein refers to devices which are able to act on body liquids. Typical actions of such devices include but are not limited to acquiring, transporting, distributing, storing, modifying, and the like. Generally, such devices include but are not limited to absorbent articles such as diapers, training pants, sanitary napkins, pantiliners, tampons, adult incontinence products, bed mats, wound plasters, sweat pads, wound covers and the like; catheters used to collect urine from bladders of mobile and immobile patients; urine collection devices such as urinals and in particular portable urinals; blood acquisition devices and saliva acquisition devices for medical uses; body liquid sampling devices; and the like.

Definition of Siphoning

The term "siphoning" refers to a process in which liquid is transported from an acquisition region along a liquid transport member to a storage region, in which the liquid transport member is substantially geometrically saturated before the intended use of the device, and in which at least a portion of the liquid acquired at the acquisition region replaces at least a part of the liquid in the liquid transport member which in turn is stored in the storage regions. Generally, storage of the liquid happens on a time scale which is much shorter than the average time interval between two subsequent loadings. In some instances, it may happen that there exists a certain delay between acquisition of liquid into the liquid transport member and storage of the replaced liquid in a storage region. Such a delay may be caused by a volume increase of the liquid transport member following acquisition of the liquid. The process of siphoning is generally reversible, i.e. the liquid may be transported in the opposite direction depending on external conditions such as applied pressure and the like. "Siphoning" as used herein includes internal siphoning as well external siphoning which processes will be defined hereinafter. In particular, the step of transporting liquid by siphoning comprises the steps of:

providing a liquid transport member being substantially geometrically saturated with liquid before the first step of acquiring liquid into the liquid transport member, the liquid saturating the liquid transport member be in liquid communication with the acquisition region;

providing a liquid storage member in liquid communication with said liquid saturating said liquid transport member, said storage member being positioned in the storage region;

acquiring liquids disposed onto the acquisition region into the liquid transport member;

replacing at least a portion of the liquid saturating the liquid transport member with the acquired liquid;

storing at least a portion of the replaced liquid in the storage member, the storage member storing the liquid by means selected from the group of capillary pressure, osmotic pressure.

The term "geometrically saturated" as used herein refers to a region of a porous material in which the liquid accessible void spaces have been filled with a liquid. The void spaces referred to in this definition are those which are present in the current geometric configuration of the porous material. In other words, a geometrically saturated device may still be able to accept additional liquid by and only by changing its geometric configuration for example by swelling, although all voids of the device are filled with liquid in the current geometric configuration. A device for handling liquids is called geometrically saturated, if all porous materials that are part of the device and intended for liquid handling are geometrically saturated.

The term "porous material" as used herein refers to materials that comprise at least two phases a solid material and a gas or void phase and optionally a third liquid phase that may be partially or completely filling said void spaces. The porosity of a material is defined as the ratio between the void volume and the total volume of the material, measured when the material is not filled with liquid. Non-limiting examples for porous materials are foams such as polyurethane, HIPE (see for example PCT patent application WO94/13704), superabsorbent foams and the like, fiber assemblies such as meltblown, spunbond, carded, cellulose webs, fiber beds and the like, porous particles such as clay, zeolites, and the like, geometrically structured materials such as tubes, balloons, channel structures etc. Porous materials might absorb liquids even if they are not hydrophilic. The porosity of the materials is therefore not linked to their affinity for the liquid that might be absorbed.

The term "substantially geometrically saturated" as used herein refers to a member in which at least 90% of the macroscopic void volume of the member are geometrically saturated, preferably at least 95% of the macroscopic void volume of the device are geometrically saturated, more preferably 97% of the macroscopic void volume of the device are geometrically saturated, most preferably 99% of the macroscopic void volume of the device are geometrically saturated.

Optionally, the step of providing a liquid transport member which is substantially geometrically saturated with liquid may comprise further individual steps. For example, the step may comprise a first step of providing a liquid transport member and a second step of activating said liquid transport member. The step of activating may comprise the step of substantially geometrically saturating the liquid transport member for example by disposing liquid onto the liquid transport member which in turn is absorbed to either liquid transport member. Alternatively, the step of activating may comprise a step of manipulating the intended acquisition region in order to render that region functional for example by removing a release paper or by wetting at least a portion of the intended acquisition region.

Optionally, the process for handling body liquids according to the present invention comprises the following further steps:

providing a liquid acquisition member acquiring body liquid into said acquisition member transporting at least a portion of said acquired body liquid into said liquid transport member.

Internal Siphoning

The term "internal siphoning" as used herein refers to a siphoning process in which the storage region is in direct liquid contact with the liquid saturating the liquid transport member. In this case, the storage member may being positioned inside the liquid transport member. Hence, such a storage member is able to directly acquire liquid from the liquid transport member and in particular that liquid which has been replaced by recently acquired liquid. Optionally, the liquid storage member in this case may also be substantially geometrically saturated with liquid before the intended use.

External Siphoning

The term "external siphoning" refers to a siphoning process in which the storage region is positioned outside of and in liquid communication with the liquid transport member. In this case, liquid be transported from the liquid transport member to the liquid storage member has to be discharged from the liquid transport member at a liquid discharge region.

Optionally, at least one of the storage regions is in direct contact with a liquid discharge region. Alternatively, the process for handling body liquid according to the present invention comprises a further step of transporting at least a portion of the liquid discharged from the liquid handling member to the liquid storage member.

Liquid Transport Member

The term "liquid transport member" as used herein refers to a device which is capable of transporting liquid from a first region to a second region.

In the following, a suitable embodiment of the liquid handling member will be described. The liquid handling member is assembled from an open celled foam material which is completely enveloped by a membrane. A suitable membrane material is available from SEFAR of Rüschlikon, Switzerland, under the designation SEFAR 03-20/14. A suitable foam material is available from Recticel of Brussels, Belgium, under the designation Bulpren S10 black. A suitable technique to completely envelope the foam material with the membrane material is to wrap the membrane material around the foam material and to subsequently heat seal all open edges of the membrane material. It will be readily apparent to the skilled practitioner to choose other similarly suitable materials. Depending on the specific intended application of the liquid handling member, it may also be required to choose similar materials with slightly different properties. After assembly, the liquid handling member is activated by immersing the liquid handling member in water or in synthetic urine until the liquid handling member is completely filled with liquid and until the membranes are completely wetted with liquid. After activation, a part of the liquid inside the liquid handling member may be squeezed out by applying an external pressure to the liquid handling member. If the activation of the liquid handling member was successful, the liquid handling member should not suck air.

Other liquid handling members suitable for the purposes of the present invention are described for example in the PCT patent application No. PCT/US98/13497 entitled "Liquid transport member for high flux rates between two port regions" filed in the name of Ehrnsperger et al. filed on Jun. 29, 1998, and in the following PCT patent applications co-filed with the present application entitled "High flux liquid transport members comprising two different permeability regions" (P&G case CM1840MQ) filed in the name of Ehrnsperger et al., "Liquid transport member for high flux rates between two port regions" (P&G case CM1841MQ) filed in the name of Ehrnsperger et al., "Liquid transport member for high flux rates against gravity" (P&G case CM1842MQ) filed in the name of Ehrnsperger et al., "Liquid transport member having high permeability bulk regions and high bubble point pressure port regions" (P&G case CM1843MQ) filed in the name of Ehrnsperger et al. All of these documents are enclosed herein by reference.

The particular geometry of the liquid handling member of the present invention can be varied according to the specific requirements of the intended application. If, for example, the liquid handling member is intended to be used in an absorbent article the liquid handling member may be defined such that its zone of intended liquid acquisition fits between the legs of the wearer and further that its intended liquid discharge zone matches the form of the storage member associated to it. Accordingly, the outer dimensions of the liquid handling member such as length, width, or thickness may also be adapted to the specific needs of the intended application. In this context, it has to be understood, however, that the design of the outer form of the liquid handling member may have an impact on its performance. For example, the cross section of the liquid handling member directly impacts on its liquid flow rates.

For application of the liquid handling member in a device for handling body liquids according to the present invention, the liquid handling member may be combined with a storage member. The term "liquid storage member" refers to a device which is capable of acquiring and storing liquid. The volume of the liquid storage member may vary with the amount of stored liquid such as by swelling. Typically, the storage member will imbibe the liquid by means of capillary suction and/or osmotic pressure. Other storage members may also use vacuum as a means to store the liquid. The liquid storage member is further capable of holding at least a portion of the stored liquid under pressure. Suitable storage members are well known in the art and may comprise for example a super absorbent polymeric material such as polyacrylate. The storage member may further comprise a fibrous structure, such as a pad of cellulosic fibers, in which the particulate superabsorbent material is dispersed. A suitable absorbent gelling material is ASAP400 available from Chemdal Ltd., United Kingdom. Further examples of suitable superabsorbent polymers, often also referred to as "hydrogel forming polymer" or "absorbent gelling material", are described in U.S. Pat. No. 5,562,646 (Goldman et al.), issued Oct. 8, 1996 and U.S. Pat. No. 5,599,335 (Goldman et al.), issued Feb. 4, 1997.

In order to pick up the liquid discharged from the liquid handling member, the storage member may be placed in direct liquid communication with the intended liquid discharge zone of the liquid handling member.

Further examples of suitable superabsorbent polymers, often also referred to as "hydrogel forming polymer" or "absorbent gelling material", are described in U.S. Pat. No. 5,562,646 (Goldman et al.), issued Oct. 8, 1996 and U.S. Pat. No. 5,599,335 (Goldman et al.), issued Feb. 4, 1997.

In one embodiment of the present invention, the liquid transport member of the present invention is geometrically saturated or substantially geometrically saturated with free liquid. The term "free liquid" as used herein refers to liquid which is not bound to a specific surface or other entity. Free liquid can be distinguished from bound liquid by measuring the proton spin relaxation time $T_2$ of the liquid molecules according to NMR (nuclear magnetic resonance) spectroscopy methods well known in the art.

Device for Handling Body Liquids

It is one aspect of the present invention to provide a device for handling body liquids which comprises a liquid transport member according to the present invention. Such devices include but are not limited to disposable absorbent articles such as baby diapers or training pants, adult incontinence products, and feminine hygiene products and other body liquid handling articles such as catheters, urinals, and the like.

In one embodiment of the present invention, the device for handling body liquids is a disposable absorbent article such as a diaper, a training pant, a sanitary napkin, an adult incontinence device, or the like. Such an absorbent article may further comprise a liquid pervious topsheet, a liquid impervious backsheet at least partially peripherally joined to the topsheet. The absorbent article may further comprise an absorbent core which may serve as a storage member for the body liquid. Topsheets, backsheet, and absorbent cores suitable for the present invention are well known in the art. In addition, there are numerous additional features known in the art which can be used in combination with the absorbent article of the present invention such as for example closure mechanisms to attach the absorbent article around the lower torso of the wearer.

What is claimed is:

1. A process for handling body liquids comprising the step of transporting said body liquids from an acquisition region to a storage region by siphoning; said step of transporting body liquid by siphoning comprising the steps of: providing a liquid transport member being substantially geometrically saturated with liquid before the first step of acquiring liquid; said liquid saturating said liquid transport member being in liquid communication with said liquid acquisition region; providing a liquid storage member in liquid communication with said liquid transport member, said liquid storage member being positioned inside said storage region; acquiring liquid disposed onto said acquisition region into said liquid transport member; replacing at least a portion of said liquid saturating said liquid transport ember by said acquired liquid; storing at least a portion of said replaced liquid in a storage member characterized in that said liquid is stored in a storage member by a means selected from the group of capillary pressure, osmotic pressure.

2. A process for handling body liquids according to claim 1 wherein the said step of providing a liquid transport member being substantially geometrically saturated liquid comprises the steps of providing a liquid transport member, and activating said liquid transport member.

3. A process for handing body liquids according to claim 2 wherein said step of activating said liquid transport member comprises a step of substantially geometrically saturating said liquid transport member.

4. A process for handling body liquids according to claim 1, wherein at least one of said storage members are positioned inside said liquid transport member, said storage members are in direct contact with said liquid substantially geometrically saturating said liquid transport member.

5. A process for handling body liquids according to claim 4, wherein at least one of said storage members is substantially geometrically saturated before the first step of acquiring liquid into said liquid handling member.

6. A process for handling body liquids according to claim 1, wherein at least one of said liquid storage members is positioned outside of and in liquid communication with the liquid transport member, said replaced liquid is discharged from said liquid transport member, at least a portion of said discharged liquid is stored in a storage member outside the liquid transport member.

7. A process for handling body liquids according to claim 6, wherein at least a portion of said replaced liquid is discharged from said liquid transport member through a liquid discharge region.

8. A process for handling body liquid according to claim 7, wherein at least one of said liquid storage members outside of said liquid transport member is in direct liquid communication with said liquid discharge region.

9. A process for handling body liquids according to claim 7 further comprising the step of transporting at least a portion of said discharged liquid from at least one of said liquid discharge regions to at least one of said storage members.

10. A process for handling body liquids according to claim 1 further comprising the steps of: providing a liquid acquisition member; acquiring body liquid into said liquid acquisition member; transporting at least a portion of said acquired liquid into said liquid transport member.

11. A device for handling body liquids having at least one liquid acquisition region and at least one liquid storage region, said storage region storing liquid by a means selected from the group of capillary pressure, osmotic pressure; said device for handling body liquids comprising a liquid transport member transporting liquid from said acquisition region to said liquid storage region characterized in that said liquid transport member is substantially geometrically saturated before the intended use of said device.

12. A device for handling body liquids having at least one liquid acquisition region and at least one liquid storage region, said storage region storing liquid by a means selected from the group of capillary pressure, osmotic pressure; said device for handling body liquids comprising a liquid transport member transporting liquid from said acquisition region to said liquid storage region characterized in that said liquid transport member is substantially geometrically saturated with free liquid.

13. A device for handling body liquids having at least one liquid acquisition region and at least one liquid storage region being spatially separated from said liquid acquisition region, said storage region storing liquid by a means selected from the group of capillary pressure, osmotic pressure; said device for handling body liquids comprising a liquid transport member transporting liquid from said acquisition region to said liquid storage region characterized in that said liquid transport member transports liquids from said liquid acquisition region to said storage region by siphoning.

14. A device for handling body liquid according to claim 13, wherein at least one of said storage regions is positioned inside said liquid transport member.

15. A device for handling body liquid according to claim 13, wherein at least one of said storage regions is positioned outside of said liquid transport member.

16. A device for handling body liquids according to claim 13, wherein said device is a disposable absorbent article.

17. A disposable absorbent article according to claim 13, wherein said disposable absorbent article is a disposable diaper.

* * * * *

UNITED STATES PATENT AND TRADEMARK OFFICE
CERTIFICATE OF CORRECTION

PATENT NO.    : 6,497,689 B1
DATED         : December 24, 2002
INVENTOR(S)   : Schmidt et al.

It is certified that error appears in the above-identified patent and that said Letters Patent is hereby corrected as shown below:

Column 8,
Line 58, please delete "claim 13" and insert therefor -- claim 16 --.

Signed and Sealed this

Thirteenth Day of July, 2004

JON W. DUDAS
*Acting Director of the United States Patent and Trademark Office*